US012616665B2

(12) United States Patent
Hasegawa et al.

(10) Patent No.: US 12,616,665 B2
(45) Date of Patent: May 5, 2026

(54) NEUTROPHIL-TO-LYMPHOCYTE RATIO DECREASING AGENT

(71) Applicants: THERABIOPHARMA INC., Kawasaki (JP); NATIONAL HOSPITAL ORGANIZATION, Meguro-ku (JP)

(72) Inventors: Koji Hasegawa, Kyoto (JP); Tadashi Hashimoto, Kawasaki (JP); Atsushi Imaizumi, Kawasaki (JP); Tatsuya Ogawa, Kawasaki (JP); Hitomi Umeta, Kawasaki (JP); Atsuhiro Kishimoto, Kawasaki (JP)

(73) Assignees: THERABIOPHARMA INC., Kawasaki (JP); NATIONAL HOSPITAL ORGANIZATION, Meguro-ku (JP)

( * ) Notice: Subject to any disclaimer, the term of this patent is extended or adjusted under 35 U.S.C. 154(b) by 449 days.

(21) Appl. No.: 18/252,553

(22) PCT Filed: Nov. 12, 2021

(86) PCT No.: PCT/JP2021/041699

§ 371 (c)(1),
(2) Date: May 11, 2023

(87) PCT Pub. No.: WO2022/102740

PCT Pub. Date: May 19, 2022

(65) Prior Publication Data

US 2024/0000723 A1 Jan. 4, 2024

(30) Foreign Application Priority Data

Nov. 12, 2020 (JP) ................................ 2020-188812

(51) Int. Cl.
*A61K 31/12* (2006.01)
*A61P 37/02* (2006.01)

(52) U.S. Cl.
CPC .............. *A61K 31/12* (2013.01); *A61P 37/02* (2018.01)

(58) Field of Classification Search
CPC ..................................................... A61K 31/12
See application file for complete search history.

(56) References Cited

U.S. PATENT DOCUMENTS

| | | | | |
|---|---|---|---|---|
| 11,986,530 | B2 * | 5/2024 | Kakeya | A61P 25/28 |
| 2011/0257126 | A1 * | 10/2011 | Neven | A61P 25/28 536/46 |
| 2012/0052095 | A1 | 3/2012 | Chaniyilparampu et al. | |
| 2019/0224325 | A1 | 7/2019 | Kakeya et al. | |
| 2020/0046651 | A1 | 2/2020 | Contractor et al. | |

FOREIGN PATENT DOCUMENTS

| | | | |
|---|---|---|---|
| JP | 2012-510466 | A | 5/2012 |
| JP | 2013-95723 | A | 5/2013 |
| JP | 2020-26434 | A | 2/2020 |
| WO | WO 2018/003857 | A1 | 1/2018 |

OTHER PUBLICATIONS

ASquaredNutrition.*
Sandur et al., Carcinogenesis, 2007, 28(8): 1765-1773.*
Sasako et al. CAS: 162: 449560, 2015.*
International Search Report mailed on Jan. 11, 2022 in PCT/JP2021/041699 filed on Nov. 12, 2021 (3 pages).
Journal of the Japan Society of Coloproctology, vol. 69, pp. 154-158, 2016.
Kermali, M. et al. “The role of biomarkers in diagnosis of COVID-19—A systematic review” Life Science, vol. 254, 2020, 117788, 13, pages.
Mazumder A. et al. “Inhibition of Human Immunodeficiency Virus Type-1 Integrase by Curcumin” Biochemical Pharmacology, vol. 49, No. 8. pp. 1165-1170, 1995.
Ryan, Jennifer J. et al. “Effect of a Nutrition Support Formula in Adults With Inflammatory Bowel Disease: A Pilot Study” Global Advances in Health and Medicine, Jul. 29, 2019. vol. 8. pp. 1-8. DOI: 10.1177/2164956119867251.
Kishimoto, Atsuhiro et al. “Newly Developed Highly Bioavailable Curcumin Formulation, curcuRouge™, Reduces Neutrophil/Lymphocyte Ratio in the Elderly: A Double-Blind, Placebo-Controlled Clinical Trial” J. Nutr. Sci. Vitaminol, Aug. 31, 2021, vol. 67. pp. 249-252.
Sunagawa, Yoichi et al. “A novel amorphous preparation improved curcumin bioavailability in healthy volunteers: A single-dose, double-blind, two-way crossover study” Journal of Functional Foods, Apr. 7, 2021, vol. 81, 2021, 104443. pp. 1-8.

* cited by examiner

*Primary Examiner* — Rei Tsang Shiao
(74) *Attorney, Agent, or Firm* — Oblon, McClelland, Maier & Neustadt, L.L.P.

(57) ABSTRACT

Provided is an agent or a food composition capable of decreasing a neutrophil-to-lymphocyte ratio. An agent for decreasing a neutrophil-to-lymphocyte ratio in blood contains a curcumin as an active ingredient.

2 Claims, No Drawings

NEUTROPHIL-TO-LYMPHOCYTE RATIO DECREASING AGENT

FIELD OF THE INVENTION

The present invention relates to an agent for decreasing a neutrophil-to-lymphocyte ratio in blood.

BACKGROUND OF THE INVENTION

A white blood cell is an immunocompetent cell involved in biophylaxis, and for example, eliminates foreign substances such as bacteria and viruses that have entered the body from the outside of the body, and eliminates a tumor cell and a cell that has finished a role thereof. There are five types of white blood cells: a monocyte, a lymphocyte, a neutrophil, a basophil, and an eosinophil.

Among these, a lymphocyte is divided into a natural killer cell, a T cell, and a B cell, and has a function of attacking small foreign substances such as viruses and a tumor cell in particular. On the other hand, a neutrophil exhibits migration to an inflammatory cytokine, bacteria, and fungi, gathers in sites of inflammation, phagocytoses, kills, and degrades foreign substances such as bacteria and fungi, and protects a living body.

As described above, a neutrophil and a lymphocyte have different roles, the number of lymphocytes does not change much, and the number of neutrophils is increased by, for example, bacterial infection, inflammation, and cancer.

In recent years, it has been reported that a high neutrophil-to-lymphocyte ratio is involved in prognosis of various diseases such as breast cancer, large bowel cancer (Non Patent Literature 1), diabetes, or coronary artery disease, or chronic inflammation such as bacterial/viral infection, particularly COVID-19 (new coronavirus infection), in which chronic inflammation is involved. In addition, a Rotterdam study (epidemiological survey) targeting general residents of 45 years old or older also indicates that a high neutrophil lymphocyte ratio leads to a shorter life span.

In recent years, it has been revealed that curcumin has pharmacological actions such as a tumorigenesis inhibitory action, an antioxidant action, an anti-inflammatory action, a cholesterol-lowering action, an anti-allergic action (for example, an anti-IL-6 action), a brain disease preventive action, and a heart disease preventive and therapeutic action, and use of curcumin in, for example, pharmaceuticals, foods, and cosmetics has been studied
(Patent Literature 1).

Mazumdar A. et al. have reported an HIV inhibitory action of curcumin (Non Patent Literature 3).

CITATION LIST

Patent Literature

Patent Literature 1: JP 2013-95723 A

Non Patent Literature

Non Patent Literature 1: Journal of the Japan Society of Coloproctology 69: 154-158, 2016
Non Patent Literature 2: Life Science 254(2020)117788
Non Patent Literature 3: Biochem. Pharmacol. 1995, 49: 1165-1170

SUMMARY OF THE INVENTION

However, a drug capable of decreasing a neutrophil-to-lymphocyte ratio has not yet been found.

Therefore, an object of the present invention is to provide an agent or a food composition capable of decreasing a neutrophil-to-lymphocyte ratio.

Therefore, the present inventor continuously administered a component confirmed to have high safety to a relatively old human and measured a change in neutrophil-to-lymphocyte ratio. As a result, the present inventor found that a curcumin has an effect of strongly decreasing a neutrophil-to-lymphocyte ratio in blood, and completed the present invention.

That is, the present invention provides the following inventions [1] to [18].

[1] An agent for decreasing a neutrophil-to-lymphocyte ratio in blood, containing a curcumin as an active ingredient.

[2] The agent for decreasing a neutrophil-to-lymphocyte ratio in blood according to [1], in which the curcumin is one or more selected from curcumin, a curcumin derivative, and a conjugate of curcumin or a curcumin derivative and a water-soluble substance.

[3] The agent for decreasing a neutrophil-to-lymphocyte ratio in blood according to [2], in which the curcumin derivative is one or more selected from bisdemethoxy curcumin, demethoxy curcumin, and tetrahydrocurcumin.

[4] The agent for decreasing a neutrophil-to-lymphocyte ratio in blood according to [2], in which the water-soluble substance is one or more selected from glucuronic acid, sulfuric acid, glutathione, and amino acid.

[5] The agent for decreasing a neutrophil-to-lymphocyte ratio in blood according to [2], in which the water-soluble substance is one or more selected from glucuronic acid and sulfuric acid.

[6] The agent for decreasing a neutrophil-to-lymphocyte ratio in blood according to [1], in which the curcumin is curcumin monoglucuronide.

[7] A food composition for decreasing a neutrophil-to-lymphocyte ratio in blood, containing a curcumin.

[8] The composition according to [7], in which the curcumin is one or more selected from curcumin, a curcumin derivative, and a conjugate of curcumin or a curcumin derivative and a water-soluble substance.

[9] The composition according to [8], in which the curcumin derivative is one or more selected from bisdemethoxy curcumin, demethoxy curcumin, and tetrahydrocurcumin.

[10] The composition according to [8], in which the water-soluble substance is one or more selected from glucuronic acid, sulfuric acid, glutathione, and amino acid.

[11] The composition according to [8], in which the water-soluble substance is one or more selected from glucuronic acid and sulfuric acid.

[12] The composition according to [7], in which the curcumin is curcumin monoglucuronide.

[13] A curcumin used for decreasing a neutrophil-to-lymphocyte ratio in blood.

[14] The curcumin according to [13], in which the curcumin is one or more selected from curcumin, a curcumin derivative, and a conjugate of curcumin or a curcumin derivative and a water-soluble substance.

[15] Use of a curcumin for manufacturing an agent for decreasing a neutrophil-to-lymphocyte ratio in blood.

[16] The use according to [15], in which the curcumin is one or more selected from curcumin, a curcumin derivative, and a conjugate of curcumin or a curcumin derivative and a water-soluble substance.

[17] A method for decreasing a neutrophil-to-lymphocyte ratio in blood, characterized by administering an effective amount of a curcumin.

[18] The method according to [17], in which the curcumin is one or more selected from curcumin, a curcumin derivative, and a conjugate of curcumin or a curcumin derivative and a water-soluble substance.

Advantageous Effects of the Invention

When a curcumin is administered, a neutrophil-to-lymphocyte ratio in blood decreases. Therefore, prognosis of a disease afflicted by a patient with a high neutrophil-to-lymphocyte ratio can be improved. Examples of such a disease include an allergic disease such as asthma or atopic dermatitis, an autoimmune disease such as rheumatoid arthritis, arteriosclerosis, a cardiovascular disease, heart failure, a kidney disease, Alzheimer's disease, a severe infection such as sepsis or pneumonia, rheumatic fever, a malignant tumor, chronic myeloproliferative leukemia, polycythemia vera, essential thrombocythemia, myelofibrosis, and a viral infection such as severe acute respiratory syndrome (SARS), middle east respiratory syndrome (MERS), or COVID-19 (BARS-Cov-2). Prognosis of these diseases can be improved.

DETAILED DESCRIPTION OF THE INVENTION

An active ingredient of each of an agent for improving a neutrophil-to-lymphocyte ratio in blood and a food composition for improving a neutrophil-to-lymphocyte ratio in blood of the present invention is a curcumin.

Examples of the curcumin include one or more selected from curcumin, a curcumin derivative, and a conjugate of curcumin or a curcumin derivative and a water-soluble substance.

Curcumin is a main component of curcuminoid contained in a turmeric pigment and is a compound represented by the following structural formula (1).

(1)

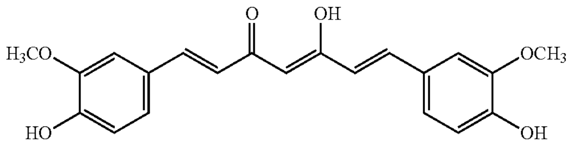

Examples of the curcumin derivative include bisdemethoxycurcumin, demethoxycurcumin, and tetrahydrocurcumin.

As curcumin in the present invention, chemically synthesized curcumin may be used, or curcumin distributed as a turmeric pigment may be used. Examples of the turmeric pigment include: turmeric powder obtained by powdering a dried rhizome of turmeric belonging to the ginger family (Curcuma longa Linne); crude curcumin or oleoresin (turmeric oleoresin) obtained by extracting the turmeric powder using an appropriate solvent (for example, ethanol, oil and fat, propylene glycol, hexane, or acetone); and purified curcumin.

Note that curcumin includes both keto type curcumin and enol type curcumin which are tautomers.

Examples of a water-soluble substance in the conjugate of curcumin or a curcumin derivative and the water-soluble substance of the present invention include one or more selected from glucuronic acid, sulfuric acid, glutathione, and amino acid. Examples of the amino acid include an amino acid present in a living body, for example, an essential amino acid.

For example, the conjugate of curcumin and a water-soluble substance can maintain a concentration of free curcumin in blood at a high value. As a result, a pharmacological action of curcumin can be sufficiently obtained. In addition, the conjugate of curcumin and a water-soluble substance is an in vivo metabolite of curcumin, and therefore has very high safety, which is preferable.

A bonding molar ratio between curcumin and the water-soluble substance is preferably curcumin:water-soluble substance=1:1 to 1:3, more preferably 1:1 to 1:2, and even more preferably 1:1.

A conjugated form (bonding form) between curcumin and the water-soluble substance is, for example, a form of formula (2).

(2)

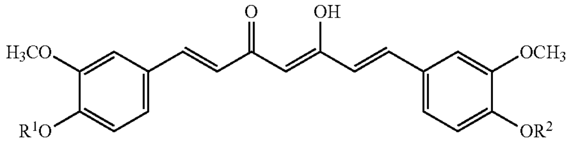

(In the formula, at least one of $R^1$ and $R^2$ is a residue of the water-soluble substance, and the remainder is a hydrogen atom.)

In the formula (2), one or both of $R^1$ and $R^2$ are preferably a glucuronic acid residue or a sulfuric acid residue, and the remainder is preferably a hydrogen atom. In particular, curcumin monoglucuronide in which $R^1$ is a glucuronic acid residue and $R^2$ is a hydrogen atom is more preferable.

The conjugate of curcumin and a water-soluble substance can be manufactured by a method described in WO 2018/003857 A.

The curcumin has an effect of strongly decreasing a neutrophil-to-lymphocyte ratio in blood as described in Examples below. Therefore, an agent for decreasing a neutrophil-to-lymphocyte ratio in blood and a food composition for decreasing a neutrophil-to-lymphocyte ratio in blood, containing the curcumin, have an action of improving prognosis of a disease having a high neutrophil-to-lymphocyte ratio in blood.

Here, examples of a disease whose prognosis is highly likely to be improved include an allergic disease such as asthma or atopic dermatitis, an autoimmune disease such as rheumatoid arthritis, arteriosclerosis, a cardiovascular disease, heart failure, a kidney disease, Alzheimer's disease, a severe infection such as sepsis or pneumonia, rheumatic fever, a malignant tumor, chronic myeloproliferative leukemia, polycythemia vera, essential thrombocythemia, myelofibrosis, and a viral infection such as severe acute respiratory syndrome (SARS), middle east respiratory syndrome (MERS), or COVID-19 (SARS-Cov-2).

In addition, the curcumin has already been widely used as a functional food, and has been confirmed to have high safety.

The content of the curcumin in each of the agent and the composition of the present invention cannot be generally determined, and is, for example, preferably from 1 to 100% by mass, more preferably from 5 to 100% by mass, and even more preferably from 10 to 100% by mass.

As an administration route of the agent for decreasing a neutrophil-to-lymphocyte ratio in blood of the present invention, any of systemic administration, local administration, an oral route, and a parenteral route can be selected depending on, for example, a disease or a symptom. Oral administration in a form of a suitable dosage form, for example, a tablet, a pill, a capsule, a granule, a powder, or a liquid, or parenteral administration in a form of an injection (for example, intravenous injection or intramuscular injection), a suppository, a transdermal agent, a nasal agent, or an inhalant can be selected depending on an administration method and route.

A formulation for oral administration according to the invention can be a solid formulation such as a tablet, a capsule, a powder, or a granule. Such a formulation is manufactured according to a conventional method by mixing one or more active substances with, for example, an inert excipient, lubricant, disintegrant, or solubilizer. The excipient can be, for example, lactose, cellulose, mannitol, or glucose.

The lubricant can be, for example, magnesium stearate. The disintegrant can be, for example, sodium carboxymethyl starch. The tablet or pill may be optionally coated with a sugar coating or a stomach-soluble or enteric coating agent.

A therapeutic agent for oral administration can be a liquid formulation such as a pharmacologically acceptable extract, emulsion, liquid, suspension, syrup, spirit, or elixir. Such a formulation contains a generally used inert solvent (for example, purified water or ethanol), and may further contain a solubilizing agent, a wetting agent, a suspending agent, a sweetening agent, a flavoring agent, an aromatic agent, a buffering agent (for example, sodium citrate), a stabilizer, or a preservative.

A therapeutic agent for parenteral administration can be an injection such as a sterile aqueous or non-aqueous liquid, suspension, or emulsion, an ointment and a lotion, a sublingual agent for oral cavity administration, an oral cavity patch, an aerosol for nasal administration, or a suppository.

An injection can be administered by injection into, for example, a joint, a subcutaneous, an intradermal, or an intramuscular in addition to normal intravenous administration and intraarterial administration. An aqueous solvent for an injection can be, for example, distilled water or saline. A non-aqueous solvent for an injection can be, for example, propylene glycol, polyethylene glycol, a vegetable oil such as olive oil, an alcohol such as ethanol, or polysorbate 80 (official designation). Such a formulation may further contain an isotonizing agent (for example, sodium chloride or glucose), a preservative, a wetting agent, an emulsifying agent, a dispersing agent, a stabilizer, a pH regulator (for example, sodium citrate, sodium acetate, or sodium phosphate), a buffering agent, a local anesthetic (for example, procaine hydrochloride or lidocaine hydrochloride), or a solubilizer.

These formulations can be sterilized, for example, by filtration through a bacteria-retaining filter, by blending a disinfectant, or by irradiation with radiation. In addition, a composition obtained by dissolving or suspending a sterile solid composition in sterile water or injection solvent before use can also be used as these formulations. These formulations can be manufactured by a known method usually used in a formulation step.

Examples of a form of the food composition for decreasing a neutrophil-to-lymphocyte ratio in blood of the present invention include forms such as a tablet, a pill, a capsule, a granule, a powder, and a liquid (including a drink). These forms can be manufactured in a similar manner to the formulation for oral administration described above.

A dose of the agent for decreasing a neutrophil-to-lymphocyte ratio in blood or the food composition for decreasing a neutrophil-to-lymphocyte ratio in blood of the present invention is not particularly limited, and is preferably from 10 mg to 10 g, and more preferably from 30 mg to 10 g per day for an adult as a curcumin.

EXAMPLES

Next, the present invention will be described in more detail based on Examples. However, the present invention is not limited to the Examples.

Example 1

Each of 20 men and women of 60 years old or older was caused to take a curcumin-containing capsule (containing 90 mg of curcumin per capsule) twice a day in the morning and the evening for four weeks (daily dose 180 mg). Venous blood was collected at start and end of administration, and a neutrophil-to-lymphocyte ratio was measured.

As a result, in a non-parametric test (Wilcoxon code rank test), the neutrophil-to-lymphocyte ratio at start of administration was 1.7 (1.3, 2.1), whereas the neutrophil-to-lymphocyte ratio at end of administration was 1.4 (1.2, 1.7). The neutrophil-to-lymphocyte ratio significantly decreased at a risk ratio of 0.02%.

The invention claimed is:

1. A method for decreasing a neutrophil-to-lymphocyte ratio in blood, the method comprising orally administering to an adult in need thereof, an agent comprising a curcumin as an active ingredient at a dose of from 30 mg to 10 g per day for at least four weeks.

2. The method of claim 1, wherein the adult in need thereof is at least 60 years old.

* * * * *